United States Patent [19]

Smyth

[11] Patent Number: 5,649,061
[45] Date of Patent: Jul. 15, 1997

[54] DEVICE AND METHOD FOR ESTIMATING A MENTAL DECISION

[75] Inventor: Christopher C. Smyth, Fallston, Md.

[73] Assignee: The United States of America as represented by the Secretary of the Army, Washington, D.C.

[21] Appl. No.: 439,392

[22] Filed: May 11, 1995

[51] Int. Cl.$^6$ .................. A61B 3/14; A61B 5/05
[52] U.S. Cl. .............. 395/20; 351/210; 250/221; 128/731; 395/21
[58] Field of Search .................. 128/731, 745; 351/218, 209; 395/20

[56] References Cited

U.S. PATENT DOCUMENTS

| | | |
|---|---|---|
| 3,986,030 | 10/1976 | Teltscher . |
| 4,109,145 | 8/1978 | Graf . |
| 4,474,186 | 10/1984 | Ledley ................... 128/733 |
| 4,610,259 | 9/1986 | Cohen ................... 128/731 |
| 4,648,052 | 3/1987 | Friedman et al. . |
| 4,859,050 | 8/1989 | Borah ................... 351/210 |
| 4,973,149 | 11/1990 | Hutchinson . |
| 5,092,343 | 3/1992 | Spitzer ................... 128/733 |
| 5,218,530 | 6/1993 | Jastrzebski ............. 364/413.05 |
| 5,417,211 | 5/1995 | Abraham-Fuchs ............. 128/653.1 |
| 5,447,166 | 9/1995 | Gevins ................... 128/731 |
| 5,481,622 | 1/1996 | Gerhardt ................... 382/103 |
| 5,491,492 | 2/1996 | Knapp ................... 345/8 |
| 5,517,021 | 5/1996 | Kaufman ................... 20/221 |

FOREIGN PATENT DOCUMENTS

| | | | |
|---|---|---|---|
| 301790 | 2/1989 | European Pat. Off. ........... A61B 5/04 |
| 6-266497 | 9/1994 | Japan ............... B42F 21/06 |

OTHER PUBLICATIONS

Adams, C. "If Looks Could Kill: The Eyes Have It." *Military & Aerospace Electronics* (1990): 35–37.

Box, G. and G. Jenkins. *Time Series Analysis, Forecasting, and Control*. Holden–Day, 1976.

Calhoun, G.; W. Janson and C. Arbak. "Use Of Eye Control To Select Switches." *Proceedings of the Human Factors Society 30th Annual Meeting* (1986).

Carpenter, P. and M. Just. "Eye Fixations During Menta Rotations." in *Eye Movements and the Higher Psychological Functions*. Edited by, J. Senders, D. Fisher and R. Monty. Lawrence Erlbaum Associates, 1978, pp. 115–133.

(List continued on next page.)

*Primary Examiner*—David K. Moore
*Assistant Examiner*—Jeffrey S. Smith
*Attorney, Agent, or Firm*—Freda L. Krosnick; Muzio B. Roberto

[57] ABSTRACT

A device and method for estimating a mental decision to select a visual cue from the viewer's eye fixation and corresponding single event evoked cerebral potential. The device comprises an eyetracker, an electronic biosignal processor and a digital computer. The eyetracker determines the instantaneous viewing direction from oculometric measurements and a head position and orientation sensor. The electronic processor continually estimates the cerebral electroencephalogramic potential from scalp surface measurements following corrections for electrooculogramic, electromyogramic and electrocardiogramic artifacts. The digital computer analyzes the viewing direction data for a fixation and then extracts the corresponding single event evoked cerebral potential. The fixation properties, such as duration, start and end pupil sizes, end state (saccade or blink) and gaze fixation count, and the parametric representation of the evoked potential are all inputs to an artificial neural network for outputting an estimate of the selection interest in the gaze point of regard. The artificial neural network is trained off-line prior to application to represent the mental decisions of the viewer. The device can be used to control computerized machinery from a video display by ocular gaze point of regard alone, by determining which visual cue the viewer is looking at and then using the estimation of the task-related selection as a selector switch.

5 Claims, 7 Drawing Sheets

OTHER PUBLICATIONS

Cerutti, S.; G. Chiarenza; D. Liberati; P. Mascellani; and G. Pavesi. "A Parametric Method of Identification of Single-Trial Event-Related Potentials in the Brain." *IEEE Transactions on Biomedical Engineering* 35, No. 9 (1988): 701–711.

Duda, R. and P. Hart. *Pattern Classification and Scene Analysis*. John Wiley & Sons, Inc., 1973.

Frost, J. and W. Shumate. "A Disposable Electrode System for EEG Monitoring During Long-Term Space Flight." In *Biomedical Electrode Technology: Theory and Practice*, Edited by, H. Miller and D. Harrison. Academic Press, Inc., 1974, pp. 377–386.

Gomer, F.; R. Spicuzza and R. O'Donnell. "Evoked Potential Correlates of Visual Recognition During Memory–Scanning Tasks." *Physiological Psychology* 4, (1976): 61–65.

Grozinger, B.; H. Kornhuber and J. Kriebel. "Human Cerebral Potentials Preceding Speech Production, Phonation, and Movements of the Mouth and Tongue, with Refernece to Respiratory and Extracerebral Potentials." in *Language and Hemispheric Specialization in Man: Cerebral Event-Related Potentials, Progress in Clinical Neurophysiology*. Edited by, J. Desmedt. Kager, Gasser & Cie Aktiengesellschaft, 1977, pp. 187–193.

Hanley, J.; P. Hahn and W. Adey. "Electrode Systems for Recording the EEG in Active Subjects." in *Biomedical Electrode Technology: Theory and Practice*. Edited by, H. Miller and D. Harrison, Academic Press, Inc., 1974, pp. 283–314.

Isaksson, A.; A. Wernberg and L. Zetterberg. "Computer Analysis of EEG Signals with Parametric Models." *Proceedings of the IEEE* 69, No. 4 (1981): 451–461.

Itakura, F. "Minimum Prediction Residual Principle Applied to Speech Recognition." *IEEE Transactions on Acoustics, Speech, and Signal Processing* 23 (1975): 67–72.

Jacob, R. What You See is What You Get: the Use of Eye Movements in Human–Computer Interaction Techniques. Naval Research Laboratory, 1989.

Jasper, H. "Report of Committee on Methods of Clinical Examination in EEG: Appendix: The Ten–Twenty Electrode System of the International Federation." *Electroencephalography and Clinical Neurophysiology* 10 (1958): 371–375.

Just, M. and P. Carpenter. "Influence Processes During Reading: Reflections from Eye Fixations." in *Eye Movements and the Higher Psychological Functions*. Edited by, J. Senders; D. Fisher and R. A. Monty. Lawrence Erlbaum Associates, 1978, pp. 157–174.

Maas, A. and M. Rodenberg. "Digital Automatic Circuit for Over–Range Correction." *Medical & Biological Engineering and Computing* 20 (Mar. 1982): 245–247.

Rabiner, L. and R. Schafer. *Digital Processing of Speech Signals*. Prentice-Hall, Inc., 1978.

Rositano, S. "Flexible Electrodes —For the Patient's Sake." In *Biomedical Electrode Technology: Theory and Practice*. Edited by, H. Miller and D. Harrison. Academic Press, Inc., 1974, pp. 81–88.

Rumelhart, D. and J. McClelland. *Parallel Distributed Processing*. The MIT Press, 1988.

Smyth, C. "The Use of Single Event Evoked Cerebral Potentials to Predict Stimulus Identifications." *34th Annual Human Factors Society Conference Proceedings* (1990): 1431–1435.

Smyth, C. and M. Dominessy. "Comparison of Oculometer and Head–Fixed Reticle with Voice or Switch and Touch Panel for Data Entry on a Generic Tactical Air Combat Display." in *U. S. Army Human Engineering Laboratory Technical Memorandum* (1989): 21–89.

Spelt, P. "Introduction to Artificial Neural Networks for Human Factors." *Human Factors Society Bulletin* 34, No. 7 (1991): 1–4.

Stern, J. "In the Blink of An Eye." *The Sciences* (Nov./Dec. 1988).

Studt, T. "Neural Networks: Computer Toolbox for the '90s." *R&D Magazine* (Sep. 1991): 36–42.

White, C. T. "Eye Movements, Evoked Responses, and Visual Perception: Some Speculations." *Acta Psychologica* 27 (1967): 337–340.

White, C. T.; C. White and R. Hintze. "Cortical and Subcortical Components of the Pattern VEP." *International Journal of Neuroscience* 19 (1983): 125–132.

White, C.; C. White and R. Hintze. "Pattern Component Ratio in Pattern Reversal VEP: Normative Data and Clinical Applications." *International Journal of Neuroscience* 19 (1983): 133–142.

White, C.; C. White and R. Hintze. "Functional Differences of Early and Late Components of Pattern–Reversal Visual Evoked Potential." In *Documenta Ophthalmologica Proceedings* 40. (Junk Publishers 1984): 293–301.

Sutter, "An oculo encephalographic communication system," Sixth annual conference on rehabilitation engineering.

Wilson, "Analyzing biological signals with CMAC, a neural network," IEEE bioengineering, 1991 17th annual northeast conference.

Anonymous, "Health: Mind reading computer," Futurist, v 26 n 3 p. 49.

Tatsumi, "Discriminant analysis of visual evoked potentials and its discrimination using neunral networks," Science Univ. of Tokyo, Faculty of Science and Technology (Institute of Electronics, information and communication engineers, vol. 89, No. 315.

Daviss, "Brain powered," Discover, v15 n5 May 1994.

DEVICE AND METHOD FOR ESTIMATING A MENTAL DECISION

BACKGROUND OF THE INVENTION

1. Field of the Invention

The present invention relates to estimating a mental decision to activate a task related function which is selected by a visual cue and, therefore, can be used to control machines from a visual display by eye gaze alone.

The present invention has many potential applications in the medical, scientific, engineering, manufacturing, military, entertainment, and other fields. The present invention may be used as a tool for medical diagnosis of ocular functions, as an aid to the paraplegic handicapped, as an instrument for providing measurement of ocular functions and workload in human factors studies, as a measure of subject training, as a tool for fatigue monitoring, as part of an electronic safety net to detect performance degradation due to pilot incapacitation in piloted and teleoperated vehicles, as a component of an electronic intelligent pilot-vehicle interface used for situation awareness aiding in piloted and teleoperated vehicles, as a tool for task scan analysis including situation awareness measuring, as a controller of machines and computer games, and for advertisement and usability analysis.

Particularly, the present invention is utilized to control computerized machines from an electronic video display by the ocular gaze point of regard alone. Examples of machine control by ocular functions are: (1) updating computer generated information displays, (2) selecting panel switches and instruments, (3) controlling the fidelity of computer generated imagery scene inserts in simulations, (4) controlling the viewing direction of remotely located cameras, (5) controlling the movement of teleoperated robotics platforms or vehicles, (6) selecting display subareas for automated scene analysis in aided target recognition, (7) designating targets from direct sight or from a sensor display, and (8) weapon system pointing.

The present invention has particular applications to time shared concurrent tasks where hands are involved in a continual time critical pilotage task and eyes are used intermittently to control a discrete task. The present invention enables both tasks to share a common visual working area with overlaid visual images. Therefore, the present invention allows task interference to be reduced by dedicating eye-movements and visual attention to the same working surface.

An example of such an application would be single pilot nap-of-earth low-level helicopter flight while updating on-board heads-up displays. A similar application is teleoperations of remote vehicles from video displays with camera control. Another such application is to the operation of completely enclosed armored vehicles with "transparent" or "see through" armor. There the operator would see a video projection of the outside scene, recorded by externally mounted cameras and relayed to internal monitors. The operator would use the present invention to control displays overlaid on the scene projection while concurrently performing the vehicle pilotage task. Similar comments apply to the piloting of "glass cockpit" designs for completely enclosed, high performance aircraft.

The present invention with a properly designed oculometer can also be used with head-mounted video displays in many application fields. The head-mounted video displays, such as those developed for virtual reality, stereographic displays, monocular or binocular vision helmet mounted displays, and night vision goggles used in piloted helicopters, vehicles, and teleoperated robotics control stations are all suitable.

2. Description of the Background Art

The conventional method of decision estimation for control of machines by ocular functions is based on measuring the eye gaze fixation duration, which commonly is longer for a visual cue of task interest than for a visual cue of disinterest. However, the statistical distributions of the interest and disinterest fixation durations tend to overlap and are clearly not separable. In practice, the user must extend the gaze duration with an unnaturally directed stare to designate a cue of interest. Usually, the user follows the display response to the cue selection with a motor action like a button push to confirm the visual selection. In some designs the user must execute an extended stare for cue selection in conjunction with the motor action to indicate a selection. This need for an extensively forced gaze tends to interrupt the task flow since any naturally occurring visual search patterns are momentarily suppressed. It can also increase ocular fatigue due to the corresponding reduction in eye blinks and the associated reductions in corneal lubrication and oxygenation. Furthermore, the need for a confirming motor action increases the workload of the viewer.

SUMMARY OF THE INVENTION

The present invention estimates a mental decision to select a visual cue of task related interest, from both eye fixation and the associated single event evoked cerebral potential. The invention uses the start of the eye fixation to trigger the computation of the corresponding evoked cerebral potential.

The design of the invention is based on the physiological evidence for the relationships existing between eye movements, evoked visual potentials and human visual information processing. This evidence is summarized as follows:

(1) While a visual cue is acquired by a rapid eye-movement known as a saccade, the cue can only be studied during a fixation lasting typically from 200 to 600 milliseconds;

(2) Simple target cues at known locations are identified within several fixations, which taken together define a gaze with the first fixation locating a critical feature of the cue and the second fixation being longer in time during which the critical feature is mentally compared;

(3) The duration of an eye fixation occurring during a mental comparison tends to be longer for a visual cue of task-interest than for a visual cue of disinterest;

(4) The evoked visual potential generated during a fixation period has waveform components which correspond to the stages of visual information processing;

(5) The amplitude of the evoked potential component occurring about 250 to 300 milliseconds is greater for a visual cue of task-interest than for a visual cue of disinterest;

(6) The eye pupil of an alert viewer in constant illumination tends to dilate at the start of information processing reaching its maximum just before decision is made, and contracts at the moment of decision making; and (7) Eye blinks appear to mark brief breaks that the brain takes at the end of each phase of a mental task, and in this way punctuate the sequence of mental events involved in acquiring and processing information.

A preferred embodiment of the present invention is directed to a device for estimating a mental decision, comprising an eyetracker, an electronic biosignal processor and a digital computer. The eyetracker determines the instantaneous pupil size and line-of-sight from oculometric measurements and a head position and orientation sensor. The biosignal processor continually estimates the cerebral electroencephalogramic potential from scalp surface measurements, following corrections for electrooculogramic, electromyogramic and electrocardiogramic artifacts. The digital computer uses an expert system program to first segregate in real time an eye fixation from the line-of-sight data and then extracts and parameterizes the corresponding single event evoked visual potential from the electroencephalogramic data. The expert system program computes the fixation start, fixation end and pupil sizes. It classifies the fixation end state as a saccade or an eye blink and groups the fixation with prior ones into a gaze point. The eye fixation properties, such as fixation-duration, pupil size change, end state and gaze fixation number, and the parametric representation of the evoked potential, are used as input to an artificial neural network, which outputs an estimate of the mental selection being made.

Conceptually, the present invention functions as a prediction machine separating the two possible visual cue selections, "select" or "reject", in a multivariate dimensional feature set space defined by the eye fixation properties and the parametric representation of the concurrent single event evoked potential generated during the visual information processing. In this way, the present invention makes use of the naturally occurring physiological processes that underline the task related decision making process, since these physiological processes are readily generated as the user looks over the scene to select display control cues. That is, the measurements of both eye fixation properties and the associated single event evoked cortical potential are used to improve the representation of the task related decision making process. This results in a more natural, task related decision making procedure with the reduced number of forced gazes required for task related selections.

Moreover, the present invention can function to control computerized machinery from a video display by ocular gaze point of regard alone. This task is accomplished by determining which visual cue the viewer is looking at and using the estimation of the task-related selection as a selector switch. In addition, it offers auto-calibration since the user can quickly and accurately go through a calibration procedure that correlates selector decisions with ocular and physiological measurements. Then the artificial neural network is trained off-line prior to application to represent the decision process of the viewer.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and, thus, are not limitative of the present invention, and wherein.

DETAILED DESCRIPTION OF THE PREFERRED EMBODIMENTS

Figure 1:
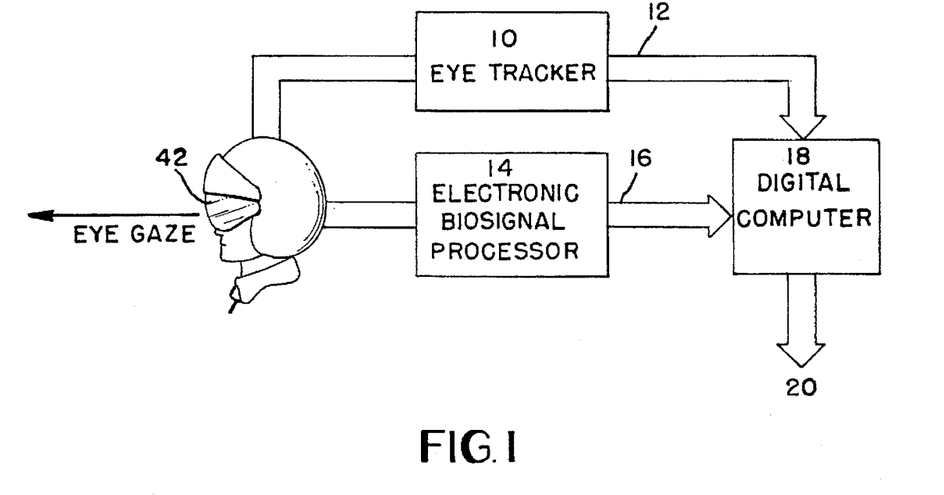
FIG. 1 is a schematic of a preferred embodiment of the present invention showing its hardware components.

Referring to the drawings and, in particular, to FIG. 1, a preferred embodiment of the present invention comprises an eyetracker 10 with a digital output 12, an electronic biosignal processor 14 with a digital output 16, and a digital computer 18 receiving the digital outputs 12,16 of the eyetracker 10 and electronic biosignal processor 14. The digital output 20 of digital computer 18 represents a decision estimate and the workspace coordinates of an eye gaze point of regard for the viewer.

Figure 2:
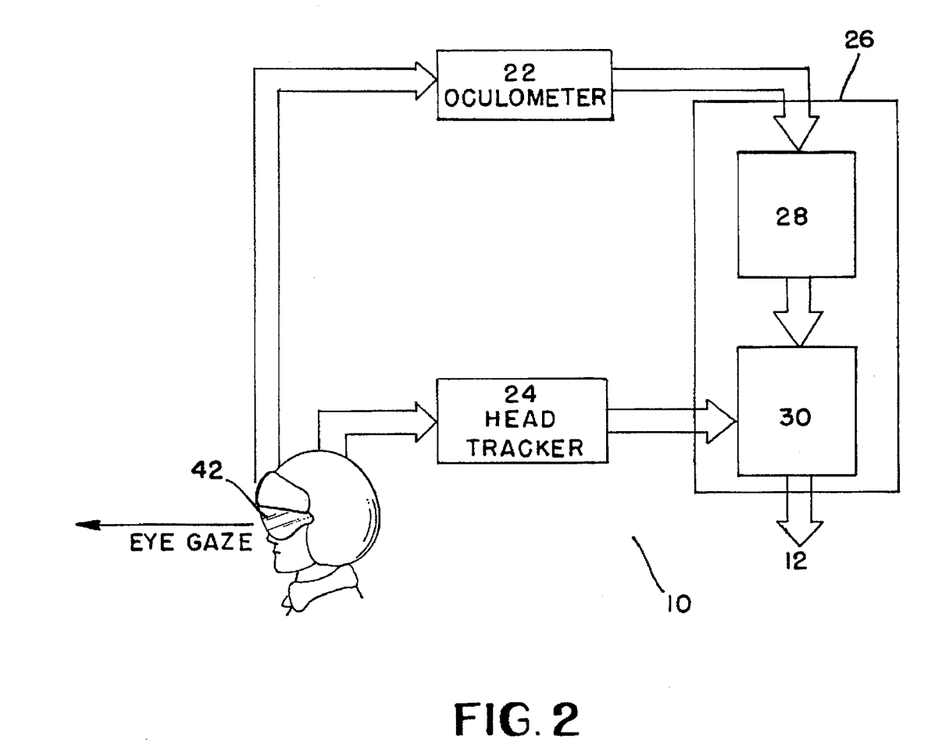
FIG. 2 is an enhanced schematic showing the hardware and software components of an eyetracker, according to the preferred embodiment of the present invention.

Referring to FIG. 2, the eyetracker 10 includes an oculometer 22, a head tracker 24 and a digital processor 26 having computer routines 28,30. The oculometer 22 measures the ocular offset and pupil size of the viewer, and has an electrical digital output to the digital processor 26. The head tracker 24 measures the head position and orientation of the viewer and has an electrical digital output to the digital processor 26. The computer routine 28 of digital processor 26 computes the visual line-of-sight from the ocular offset measurements and the routine 30 computes the workspace line-of-sight from the head tracker measurements and from the visual line-of-sight computations of routine 28. The workspace line-of-sight computations from routine 30 along with the pupil size measurements are output as digital output 12 of digital processor 26 to digital computer 18.

The oculometer 22 also measures the angular offset of the viewing direction from an angular reference system attached either to the head or fixed in the workspace. In the case where an oculometer is fixed to the head, it measures the angular offsets of the viewing direction from the reference direction in a head fixed coordinate system. The oculometer 22 functions by any of the following, well established optical measuring techniques: pupil tracking, lumbus boundary, double punkenje image, corneal reflections or retinal image. To measure head-fixed ocular offset measurements, an electrooculogramic device can be used.

Additionally, an optical system is commonly used for the pupil size measurements and eye blink determination. In this embodiment, a charge-coupled device (CCD) is used to accumulate an image of the eye which is downloaded to an image frame grabber and then piped to an image processing board. Here the centroid of the pupil image is computed using a binarization and image brightness threshold technique; the pupil diameter is computed from the centroid major and minor axes.

The head tracker 24 measures the position and orientation of the viewer's head in the workspace coordinate system. The head tracker 24 includes a source, sensor, and a processor. The sensor of the head tracker 24 is commonly attached to the head and the source is fixed in the workspace. The processor of the head tracker 24 continually computes the position and orientation of the sensor in a spatial coordinate system located by the source, and controls the transmission of the digital output data based on the computations. The head tracker 24 allows continual tracking of its sensor in all six degrees of spatial freedom, and the head tracker 24 functions by any of the following, well established techniques: magnetic source field and sensor, infrared light sources triangulation, or ultrasonic source and sensors. Some optical trackers can be fixed in the workspace and use a feedback servomechanism to center a camera on the pupil image; ranging to the eye can be achieved by dynamically focusing the pupil image or by using ultrasonic reflections from the eye.

For an oculometer fixed to the head, routine 28 of the digital processor 26 transforms the ocular offset measured by the oculometer to a viewing point and direction in the head fixed coordinate system. Such line-of-sight coordinates are in turn transformed by routine 30 into the workspace fixed coordinate system using the head position and orientation measurements from the head tracker 24. However, for an occulometer fixed in the workspace, these transformations are not necessary since the ocular offset measurements are already in the workspace coordinate system. In such cases, the digital processor 26 uses the reading of the head tracker 24 to provide feedback to the servomechanism for directing the optics of the oculometer toward the viewer's eye.

Figure 3:
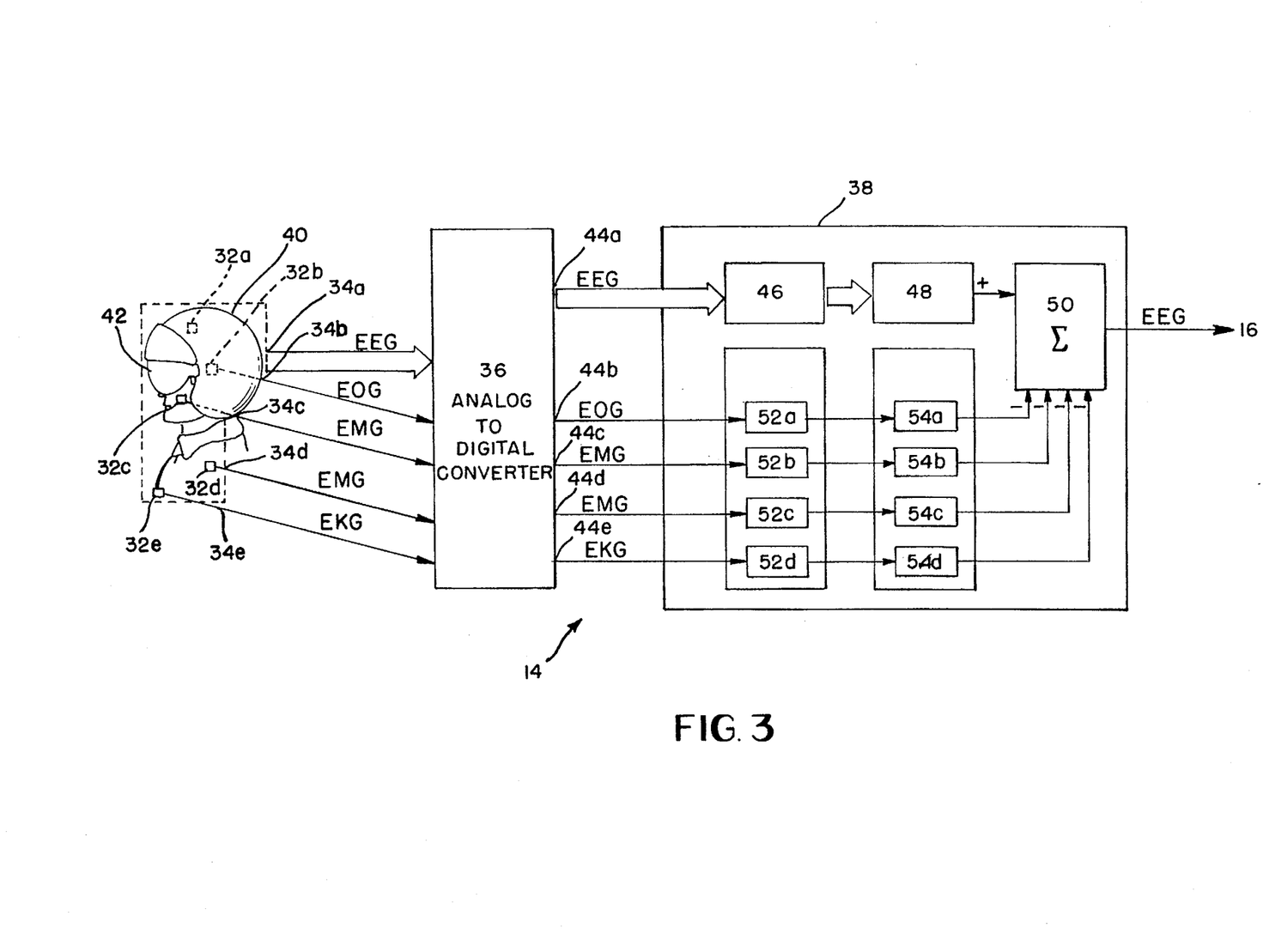
FIG. 3 is an enhanced schematic showing the hardware components of an electronic biosignal processor, according to the preferred embodiment of the present invention.

Referring to FIG. 3, the electronic biosignal processor 14 according to the present invention, continually estimates the electroencephalogram (EEG) from scalp surface analog potential measurements following corrections for electrooculogramic (EOG), electromyogramic (EMG), and electrocardiogramic (EKG) cerebral artifacts. The components of the biosignal processor 14 include arrays of skin-surface electrodes 32a–32e and electronic instrumentation amplifier modulars 34a–34e with analog outputs, a multiplexed analog-to-digital (A/D) converter 36 with analog inputs and digital outputs, and a digital signal processor 38 with digital output 16. The array of scalp skin surface electrodes 32a, electrically connected to the electronic instrumentation amplifier modular 34a, measure cerebral EEG potentials, whereas the array of skin surface electrodes 32b–32e, electrically connected to the electronic instrumentation amplifier modulars 34b–34e, measure the electrooculogramic, electromyogramic and electrocardiogramic potentials.

In a further embodiment, the skin-surface electrodes 32a used to measure the cerebral EEG potentials with the amplifier modular, are in a multiple array configuration embedded in a helmet design 40 including an indifferent electrode and amplifier ground. The electrode array is centered about the central and parietal cerebral scalp sites to reduce artifacts from extracerebral sources while maximizing reception of the visually evoked cerebral potentials. These electrodes are recessed in the helmet 40 and employ a gel impregnated floating sponge as a bridge to the scalp skin surface.

The Electromyographic, Electrocardiographic and Electrooculographic cerebral artifact potentials sources are measured by amplifier modulars 34b–34e with a battery of skin-surface electrode pairs. These extracerebral potentials, on the order of millivolts, contaminate the cerebral signals. Thus, these measurements are used to make correlating corrections to the contaminated cerebral signals.

Several electrodes 32c,32d are used to measure pertinent Electromyographic (EMG) signals generated by facial, shoulder, and arm muscles. These Electromyograms are measured using skin surface bipolar electrode-sensors adhered to the skin of the viewer over the appropriate muscle sites. In keeping with advanced electrode measuring techniques, the electrode-sensors are made from woven, stretchable, nylon fabric impregnated with silver particles. The ohmic resistance of this material is very low and stable, and the lead wire bonding is achieved by use of a conductive epoxy. This type of fabric sensor conforms easily to body contours, and its lightness and flexibility allows the user to wear the electrodes for long periods without discomfort. Also, a porous fabric supporting an electroconductive gel is placed between the skin and electrode material. The fabric is gelled at the electrode contact points.

The Electrocardiogram (EKG) is measured by amplifier modular 34e with an augmented unipolar electrode Einthoven's triangle chest cluster with amplifier ground. Such a configuration is commonly used with exercising subjects. The Electrocardiogramic (EKG) potential generated by the heart muscle is another major source of cerebral potential contamination measured by amplifier modular 34e. As described above, the electrode-sensor 32e used to measure EKG is made from woven, stretchable, nylon fabric impregnated with silver particles. A porous fabric supporting an electroconductive gel is placed between the skin and electrode material. The fabric is gelled at the electrode contact points.

The Electrooculogram (EOG) is measured by amplifier modular 34 with a periocular electrode array about the eyes of the viewer, with electrodes 32b, two electrodes located horizontally at opposing temporal cnthi sites and two more electrodes located vertically at opposing sites above the eyebrow and below an eye of the viewer. The Electrooculogram (EOG) generated by the retinal to corneal electrostatic potential of the eye, is a major source of cerebral potential contamination. This is especially true for vertical eye movements with upper eye lid lag overshoots. Horizontal eye movements contribute reduced artifacts.

Additional contamination is contributed by eye blinks. The artifacts are strongest at the frontal EEG derivations; however, some contamination occurs at the central and parietal derivations. The signals vary with frequency and are strongest in the delta and theta frequency bands. The skin surface electrode configuration for the measurement of the vertical and horizontal Electrooculogramic signals is made from conductive cloth electrode sensors. As described above, the electrode-sensors are made from woven, stretchable, nylon fabric impregnated with silver particles, and a porous fabric supports an electroconductive gel placed between the skin and electrode material.

In a still further embodiment, these electrode-sensors for measuring EOG are embedded in a neoprene holder which fits around the eyes like a set of goggles 42. The fabric of the sensors is shaped as an insert to the inner surface of the goggles 42 and is gelled only at the electrode contact points. As with all skin-surface electrode placements, the user applies a skin preparation to the skin surface to remove skin oil and outer dead skin cells before fitting the electrode support fixture, to reduce skin resistance to an acceptable level (below 3K ohms).

The amplifier modulars 34a–34e contain dual input differential instrumentation preamplifiers referenced to an indifference electrode, for amplifying the microvolt signals measured by the electrode configurations. The preamplifiers are input buffered for high input impedance with high gain, low noise, and appropriate isolation to safeguard the user from electrical shock. The electrode lead wires are twisted and the components of these amplifier modulars 34a–34e are housed in a shielded enclosure to reduce interference from outside sources of electromagnetic energy. Because of the microvolt signals, a summing amplifier is used to reduce the common-mode response to the direct current (DC) offset potential induced at the interface between the electrodes and skin surface. This potential is stable for proper electrode preparation and application. As is common practice for low signal amplifier circuits, the output of the summer is further amplified by a second stage programmable gain amplifier. After the second stage amplification, the signal is high-passed filtered (0.1 Hz cutoff) to remove electrode offset potential and low-passed filtered to remove externally induced noise.

In a further embodiment, a notch filter at power line frequency is added, although this distorts the measured signals. For user's safety, the amplifier stages are powered by batteries at the amplifier site, and their outputs are transmitted through optocouplers to provide isolation from other power supplies.

The circuit design for differential instrumentation amplifier used to measure the horizontal and vertical Electrooculograms, includes an ocular direct current (DC) bias correction circuit. In practice, the DC offsets generated by the corneal to retinal potentials will change with light adaptation, and thereby drifting over time out of range of the power supplies results in clamped amplifiers. For these reasons, the DC bias correction voltage for the summing amplifier is continually updated by an automatic digital circuit for over-range correction.

Once the amplified skin surface electrode voltage measurements from the instrumentation amplifier modulars 34a–34e are obtained, these measurements are input as analog inputs to the multiplexed analog-to-digital (A/D) converter 36 where the signals are digitized for further processing. The digitized signal outputs 44a–44e from the A/D converter 36 are input to a digital signal processor 38 which, in turn, performs several digital filtering operations on the input signals. The digital signal outputs 44a for the cerebral signals from the modular 34a are input to a programmable estimator filter 46 in series with a predictor filter 48, which is coupled to a positive input of a digital signal summer 50. The digital signal outputs 44b–44e for the artifact signals from the modulars 34b–34e are input to an array of programmable estimator filters 52a–52d and predictor filters 54a–54d in series, with output being corrective inputs to the digital signal summer 50. The output 16 of the summer 50 is the estimated EEG signal, which is input to computer 18.

The estimator filter 46 estimates the true EEG signals from the outputs 44a from the amplifier modular 34a, correcting for the measurement noise. The filter 46 uses the corresponding present digital output values (present measurements), past estimated values and an estimate of the measurement process noise power in the computation of the true signal estimates to estimate the true EEG signals. The filter 46 for each measurement channel, combines the previous estimate with the current measurement to account for the relative accuracies of the two quantities. In a further embodiment, the estimator filter 46 is a recursive predictor-corrector Kalman filter. This filter is programmable and the filter coefficients are determined in calibration prior to application.

The predictor filter 48 spatially smooths the background EEG signals and enhances the evoked signal. In a further embodiment, the predictor filter 48 combines the digital outputs of the estimator 46 for the cerebral EEG signals, into a sequence of weighted summations to reduce the background common to all electrode-sensors and to enhance the differences. The value of the weight for each electrode is determined by the spatial location on the scalp according to appropriate two-dimensional templates. The application of these templates results in a digital signal output with reduced extracerebral and background EEG components and enhancement of the localized evoked potential signal.

The estimator filters 52a–52d estimate the true extracerebral artifact signals from the outputs 44b–44e from the amplifier modulars 34b–34e, correcting for the measurement noise. Each of the estimator filters 52a–52d use the corresponding present digital output value (present measurement), past estimated values and an estimate of the measurement process noise power in the computation of the true signal estimate. These estimator filters 52a–52d combine the previous estimate with the current measurement to account for the relative accuracies of the two quantities. In a further embodiment, the estimator filters 52a–52d are recursive Kalman filters. Such filters are programmable and their filter coefficients are determined in calibration prior to application.

The predictor filters 54a–54d predict the components of the extracerebral artifacts in the cerebral signal contributed by the artifact sources. The filters 54a–54d act as smoothers accounting for the delay lag and attenuation in skull propagation of the artifact signals, and maintain running files of the signal values which are updated at each sampling clock cycle. The filters 54a–54d are programmable and their filter coefficients are determined in calibration prior to application. While the digital output for the filtered cerebral signal from the estimator filter 46 is a positive input to the summer 50, the digital outputs from the predictor filters 54a–54d are negative inputs to the summer 50. As a result, the summer 50 generates the output 16 which is an estimate of the EEG signal free of extracerebral artifacts.

Figure 4:
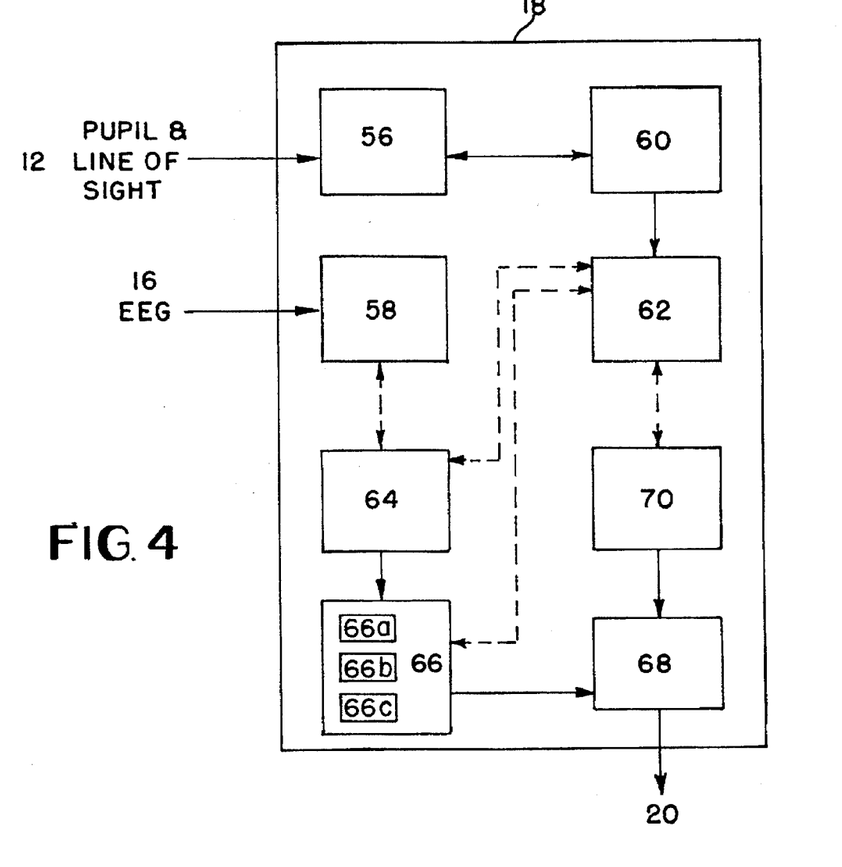
FIG. 4 is a block diagram showing the software routines of a digital computer, according to the preferred embodiment of the present invention.

Referring to FIG. 4, the digital outputs 12,16 respectively representing the workspace line-of-sight and pupil size data from the digital processor 26 and the estimated EEG signal data from the digital signal processor 38, are input to the digital computer 18 having a plurality of routines. The digital computer routine 56 reads the workspace line-of-sight and eye pupil size data from digital output 12 of the processor 26 into a memory buffer ordered by time-code. Similarly, digital computer routine 58 reads the EEG data from digital output 16 of the processor 38 into a memory buffer ordered by time-code.

The digital computer routine 60 categories the eye sight state as saccadic or fixation (either static or pursuit) from the received workspace line-of-sight data and in the process groups the fixations into gaze points. If a fixation is found, routine 60 isolates the start and end of the fixation, computes the resulting fixation duration, extracts the start and end pupil sizes, and determines the end state as saccade or blink. The routine 60 of digital computer 18 next stores the values for the fixation parameters, such as duration, pupil sizes, end state and gaze fixation count, in global common storage 62 along with the gaze viewing point and direction, and sets a software interrupt service call for digital computer subroutines to: (1) isolate the corresponding evoked potential from the EEG and (2) compute the workspace gaze point of regard.

In response to the software interrupt call, the computer routine 64 first extracts the single event transient evoked potential for the gaze fixation from the received time-coded EEG data and the start and end times of the fixation found in global common storage 62. Then it computes a parametric representation of the transient evoked potential using filtering techniques. The output of routine 64 is the parametric representation of evoked visual potential over the fixation duration. The routine 64 next calls on an expert system routine 66 passing these values on in the process.

The expert system routine 66 computes an estimate of the task-related selector decision. The routine 66 employs an artificial neural network (ANN) to represent the decision process using as input the eye gaze fixation properties, such as duration, pupil size change, the end state and the gaze fixation count, and the parametric coefficients for the corresponding single event evoked potential. Thus the routine 66 generates the estimate of the task selection which is input to an output routine 68 of digital computer 18.

Also in response to the software interrupt service call from routine 60, a computer routine 70 of digital computer 18 computes the workspace coordinates of the gaze point of regard for the fixation held in global common storage 62, from the gaze viewing point and direction, and a digitally stored data base on the workspace geometry. Thus, the routine 70 outputs the workspace coordinate data of the gaze point which is input to output routine 68. Accordingly, the output 20 of computer 18 from the output routine 68 represents the combined output of the artificial neural network of computer routine 66 for the estimation of the mental decision for task selection of the gaze point of regard and that of computer routine 70 for the gaze point workspace coordinates.

Figure 5A:
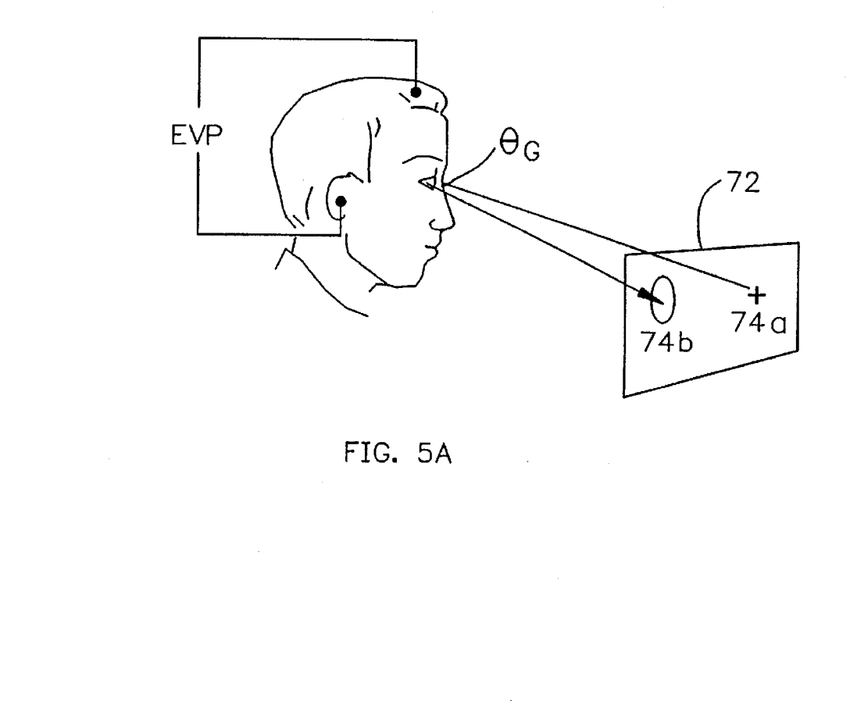
FIG. 5A is a schematic and FIG. 5B is a set of idealized plots, together showing a relationship between the ocular fixation and the transient evoked visual potential, according to the preferred embodiment of the present invention.
Figure 5B:
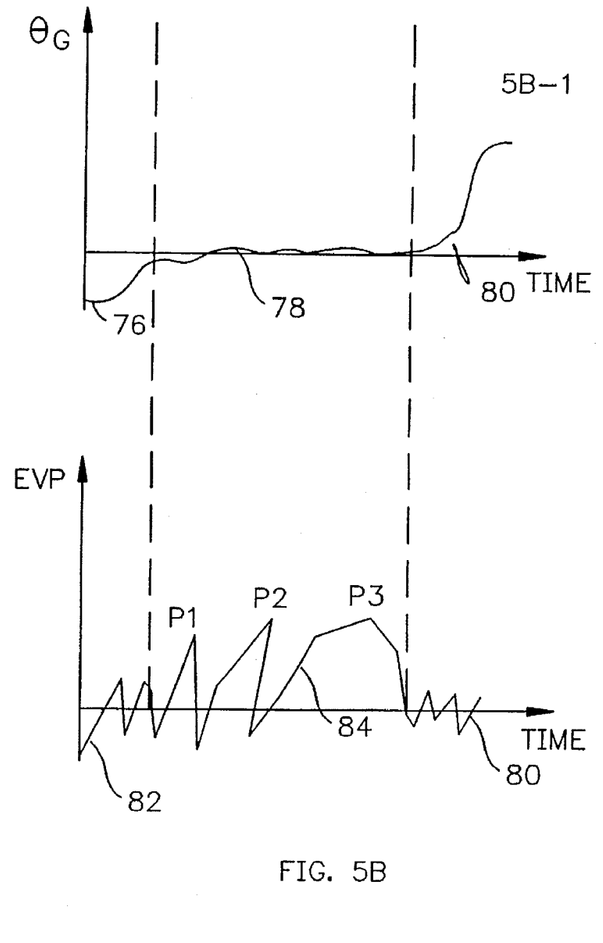

Referring to FIGS. 4, 5A and 5B in describing the relationship between ocular fixation and its transient evoked potential (EVP), the computer routine 60 of digital computer 18 isolates fixations from the line-of-sight data by classifying the immediate visual state defined by the workspace viewing direction, as fixation, saccade, pursuit or blink from an embedded expert knowledge base on these ocular states. The computer routine 60 as an expert system functions from a preprogrammed understanding of the visual process. For example, when studying a static visual display 72, the eye of the viewer is continually rotating and fixating different portions of the scene 74a and 74b. For this reason, the eye gaze on the display 72 includes sudden saccadic jumps with interposed slightly jittery fixations, which generate saccadic jump signals 76, 80 and jittery fixation signals 78, as shown in FIG. 5B; $\theta_G$ represents degrees in eye rotation of the viewer.

The saccadic jumps which move the eye of the viewer between fixations are sudden and rapid ballistic movements lasting about 30 to 120 milliseconds and traversing 15 to 40 degrees. The peak velocity for a 10 degree saccade can reach 450 degrees per second; the peak velocity for a 20 degree saccade can range from 290 to 400 degrees per second. Before another saccade can be executed, a 200 millisecond refractory period is required for recovery. Vision is suppressed during a saccade.

The fixation following a saccade is a brief period of relative stability which allows that portion of the scene within the foveal vision to be studied. The fixation period is typically from 200 to 600 milliseconds. Small jittery motions occur during a fixation and these motions are composed of slight drifts with amplitudes less than one degree, followed by microsaccadic corrections. Here, a low amplitude, high frequency tremor is superimposed. The purpose of a saccade is to rotate the eye so that the image of a cue in the visual scene falls within the foveal vision. The image is then studied during the fixation. The microsaccadic movements induce changes in the image required for seeing. However, the eye seldom remains in one fixation for a long time.

On the other hand, pursuit movements are slow involuntary eye tracking movements which smoothly follow a moving object of interest in the visual field. Pursuit movements have an initial reaction time of 0.12 to 0.25 seconds and are limited to a maximum velocity of 25 to 30 degrees per second. While the saccadic control system acts as position servomechanism directing the fovea of the eye to a target, the pursuit system acts as a velocity servomechanism rotating the eye at the same angular rate as a target.

Finally, blinks start slightly before or simultaneously with upward directed saccades, but never after the eye movement. Blinks are sometimes initiated after the onset of downward directed saccades. It has been reported that only in less than one percent of blinks is there apparent eye movement. Blinks usually last from 20 to 200 milliseconds with the longest observed terminating smoothly around 300 milliseconds.

Using a computer program which implements this knowledge, the routine 60 uses an automatic fixation and saccade classification scheme operated in conjunction with a saccadic end point predictor. The routine 60 detects saccades and predicts fixation end points, as well as separate saccades from pursuit eye tracking of moving targets and eye blinks. Here, a classification scheme which combines two methods, the angular position variance method and the velocity detection method, can be used. The end point predictor is derived from a knowledge base on the relation between saccade peak velocity and amplitude of movement.

The position variance method is based on the expert knowledge that a fixation is characterized by relative immobility with low variance in eye movement, while a saccade is distinguished by rapid change (high variance) in position. In this method, the means and variances are computed for a sliding window of time samples in eye position. The variance of the windowed samples for a fixation is lower than an empirically determined threshold level. When a saccade occurs, the variance rises, reaching a peak and then subsides toward the fixation level again. The initiation and termination of a saccade is automatically detected by comparing the position variance to the threshold level determined in an initial calibration process. Furthermore, curve fitting to the variance function is used to make predictions about the future variance values and therefore the time and location of the next fixation. This method has a time lag attributable to the width of the sampling window.

The velocity detection method operates in parallel with the above variance method. In the velocity detection method, the eye movement speed is computed from the windowed samples by first smoothing with a low-pass digital filter to remove noise and then numerically differentiating the filter output. The computed speed is compared to an empirically determined threshold level separating saccadic movements from fixations. If the computed speed is above the threshold, it is classified as saccadic, whereas if it is less than the threshold, it is considered as fixation.

The above position variance and velocity methods give similar results. In the preferred embodiments, these two methods are combined to obtain a more reliable saccade discriminator. The combined method can be based on either the agreement between the separate threshold outputs, or more elaborately, upon saccade state-probability estimates derived from the magnitudes of the position variance and speed measurements.

The saccadic end point predictor in connection with the routine 60 is activated once a saccade is detected. This method predicting the end point of the saccadic movement from the peak velocity, discriminates between saccades and pursuit tracking. The saccadic end point predictor operates based on the expert knowledge that the eye-movement velocity function during a saccade is nearly symmetrical about a peak velocity located approximately half-way to the next fixation.

In detail, the saccadic velocity function rises above the threshold detection level, accelerates to a peak velocity about half-way to the next fixation, and then decelerates below the threshold at the fixation point. Although it has been reported in the literature that a sine wave is a good fit for the velocity function, the function is in fact, more or less symmetrical depending upon the magnitude of the peak velocity. In actuality, the saccadal amplitude is related to the maximum velocity by an exponential function using curve fitting constants. A look-up table, which contains empirically determined correction factors, can be utilized to adjust for the asymmetry in the velocity function. These correction factors are derived in the calibration process. Therefore, by detecting the peak of the saccadal velocity, the relation to the saccadal amplitude is used to predict the termination time and location of the next fixation. When a saccadal movement is classified as not satisfying the end point predictor, it is reclassified as pursuit movement, the movements being less than 30 degrees per second. Blinks correspond to cases where no reflection points are detected due to obscuration of the cornea by the eyelid and, thus, are determined by the eye tracker 10.

As a further step in the analysis, the computer routine 60 of digital computer 18 groups the fixation data into task related visual gazes. The user tends to view a task related visual element with a sequence of fixations all in the same display area connected by small saccades. These fixations grouped together form a single gaze which more closely approximates the user's cognitive functioning. The routine 60 uses a retrospective algorithm to determine the start, continuation, and termination of each gaze as follows:

(1) a 100 millisecond sequence of eye fixations within 0.5 degrees of each other defines the start of a gaze; the gaze center is the mean of the eye fixations; and the algorithm delay of 100 milliseconds is undetectable to the user;

(2) the gaze is continued as long as eye fixations remain within one degree of the current gaze center; the gaze dwell time is the sum of the 100 millisecond start time and the current continuation time; and (3) A 50 millisecond sequence of eye positions that are beyond one degree of the current gaze defines the termination of the present gaze; a blink up to 200 milliseconds is allowed without termination.

In this manner, the routine 60 groups prior fixations with the present fixation into a gaze point and, thus, determines the number of fixations in the gaze. The routine 60 computes a moving gaze center for fixations during pursuit tracking wherein initial pursuit tracking includes a saccade to acquire the target on the fovea followed by steady tracking. A rate varying target is to be tracked with saccadic updatings in tracking rate.

In addition, the eye fixation parameters computed by routine 60, such as duration, start and end pupil size, end state and gaze fixation count, are related to the stages of information processing as follows. The sequential order of the fixation in the gaze appears to determine its role in information processing. For example, once a display icon has been located and recognized in a visual scene, the observer must identify it before a selection decision can be made. In the case of identifying simple target cues, such as alphabetic letters as a function of orientation, it has been shown that identification is made within a few fixations for targets at a known location. The first fixation is usually a search for a critical feature on the target. This is followed by a long fixation on the critical feature. It is reported that during this fixation period the critical feature of the target cue is mentally compared by transforming and confirmation operations to an internal stereotype of the target. The observer tends to fixate the location of the referral feature during this processing as the stereotype is retrieved from long-term memory into short-term memory (or working memory) and transformed for comparison.

The eye fixation duration for the mental comparison is statistically longer for visual cues of task interest as opposed to those of disinterest. Typically, fixation durations longer than 250 milliseconds are associated with visual cues of interest while shorter durations are associated with visual cues of disinterest. However, the statistical distributions of the interest and disinterest fixation durations tend to overlap and are clearly not separable.

There is evidence that pupil dilation is related to the information processing stages. For example, it has been shown that the pupil will dilate at the start of information processing reaching its maximum just before decision making, and contract at the moment of decision making. The extent of the dilation is an inverse function of the intelligence of the viewer and a direct function of the complexity of the problem to be solved. However, the pupil change is also a function of extraneous factors including ambient lighting and subject fatigue. For these reasons, pupil dilation is a valid measure of the stages of information processing only for alert users with constant illumination displays.

It is also known that the completion of a visual information process is often followed by another saccade or by a succession of eye blinks which were suppressed during the visual study phase. Eye blinks are reported to occur at transitions between stages of information processing. In particular, blinks appear to mark brief breaks that the brain takes at the end of each phase of a mental task, and in this way punctuate the sequence of mental events involved in acquiring and processing information. For this reason, the occurrence of eye blinks may punctuate the appropriate moments to measure pupil dilation in information processing. A blink indicates the moment at which the visual memory is realized and apparently when the brain anticipates no need for additional visual material. A blink seems to occur at the moment the subject stops taking in information and starts to internally process it. A human brain seems to need to pause between such significant sensory episodes, where the blink marks the pause. Thus, the processing of visual information is gated by explicit ocular movements.

Furthermore, based on expert knowledge of the relationship between the visual process and associated cortical functions, it is a design feature of the present invention to extract the single event transient evoked potential corresponding to the visual fixation using routine 64 of digital computer 18. During ocular fixation, the EEG signal is the sum of the background cerebral potentials and the evoked visual potential (EVP) associated with visual information processing. The background-EEG is accurately represented over a duration of several seconds as the output of an autoregressive recursire filter process (commonly on the order of 10) driven by white noise independent of the visual task.

In contrast, the EVP occurring during the fixation is a transient signal lasting less than a second. The amplitude of the background-EEG is roughly 20 microvolts. The single event EVP is on the order of 5 microvolts. The resulting signal-to-noise ratio can be as low as −30 dB. The background-EEG and the EVP are essentially uncorrelated over time, and the background-EEG is essentially noise to the EVP.

Essential to the functioning of the present invention is the relation between eye movement characteristics and the associated evoked potential (EVP). For example, the rapid movement of the eyes of the viewer from one fixation point 74a to another fixation point 74b, initiates a volley of cortical activity represented by signal 82 during each saccade signal 76 period, as shown in FIG. 5B. The brain activity during the fixation signal 78 period following a saccade is in the form of an EVP signal 84. Microsaccades occur during the fixation which may be followed by another saccade represented by signal 80 with associated cortical volley signal 86. It is as if the eye movements gate the visual data and pace the cerebral information processing during the gaze fixation.

The waveform of the EVP is known from a response to a flashing light. The waveform of the EVP includes three sequential components: the primary response period (p1: 0–90 milliseconds), the secondary response period (p2: 90–240 msecs), and the oscillatory after-discharge (p3: beyond 240 msecs). This complex pattern occurring during the 250–300 msec period is related to the assimilation of visual information.

The fixation durations reported for visual search and the corresponding EVPs suggest that the duration of 250–300 milliseconds may be critical for the processing and assimilation of visual information. The time required for the assimilation of visual information is in accord with the temporal characteristics of the EVP pattern, with full utilization of visual contour information reportedly taking 250–300 milliseconds. This is consistent with the reported fact that a person will execute about 3 fixations per second in a search, considering that the time for a saccadic movement is from 30 to 200 milliseconds.

The additional information obtained from processing evoked visual potentials (EVP) is dependent upon the variation of the signal related to information processing decisions. A variation for event averaged EVP signals averaged over many decision responses is known. Commonly, the average EVP is collected over several hundred repetitions of different test conditions. The amplitudes and latencies of the components of the average EVP waveform have been known to be correlated to the information processing stages and results. In fact, it is reported in the literature that there are significant differences in the event averaged EVP for the identification of alphabet letters as task related or not.

In an experiment, subjects when presented with a test stimulus had to decide whether or not it was one of the task related target letters which had been memorized previously, and make a choice response accordingly. It is reported that the amplitude difference between the P300 (p3) component of the event average evoked potentials (EVP) was significantly greater for learned targets than for unlearned targets. The P300 (p3) component is the positive waveform component of the event averaged EVP which follows the test stimulus by 300 milliseconds. The amplitude difference increased with the size of the learned target set.

Furthermore, while the latency of the P200 (p2) peaks remained invariant, the P300 (p3) latency increased as the size of the learned target set increased, that is, as the information processing took longer to complete. Thus, it is common practice in experiments of this nature to cue the subject when and where the target is presented to suppress eye movements during presentation. The event averaging process reduces the random background-EEG signal component thereby increasing the signal to noise ratio for the purpose of analysis.

However, while the above evidence for the relation of the evoked potential waveform (EVP) to information processing is limited to event averaged evoked signals, the present invention by design estimates a mental decision from the information in the corresponding single event evoked potential. The success of this effort depends upon the technique used to isolate the single event evoked potential (EVP) from the measured EEG signal. The form of the evoked signal is a variation of the average evoked response waveform for the task, as determined by the information processing, the decision being made, and the physiological state of the user.

In order to isolate the single event evoked potential (EVP) from the measured EEG signal, the EEG signal containing the single event evoked potential (EVP) may be mathematically described as an autoregressive process with exogenous input (an ARX process), wherein the background-EEG is the autoregressive statistical component and the evoked response is the deterministic component. The resulting mathematical expression relates the known EEG signal samples to the unknown evoked response samples and the coefficients for the autoregressive process. This expression may be solved using the Newton's iterative method of numerical analysis for solving nonlinear systems of equations. Such an iteration process will converge to a solution vector containing the evoked response samples and the autoregressive coefficients, provided that an accurate starting vector is known and the inverse of the corresponding Jacobian matrix exists in that solution.

A sensible starting vector would include average evoked response values and average autoregressive coefficients since these are closest to all feasible solutions. However, the number of unknowns can be reduced by considering the problem as being one of filter identification for a linear system corrupted by noise. The autoregressive EEG model with exogenous EVP input is mathematically equivalent to an autoregressive moving average (ARMA) filtering process with a white noise input, commonly used in system identification.

Figure 6:
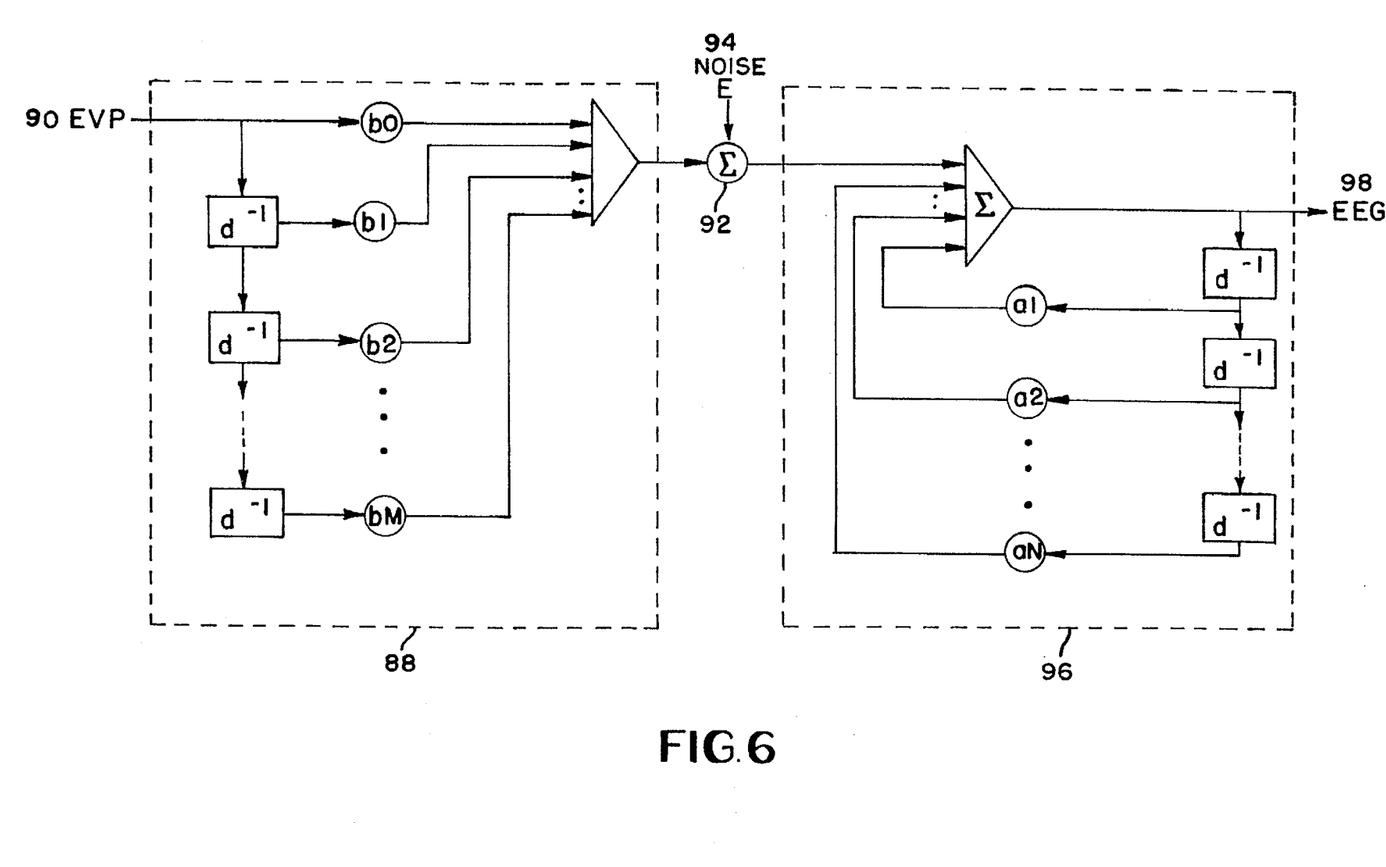
FIG. 6 is a schematic of an autoregressive, moving average (ARMA) recursive filter model for an electroencephalogramic (EEG) signal, according to the present invention.

Referring to FIG. 6, which shows an ARX recursive filter model for EEG signal, the non-recursive moving average filter 88 filters the deterministic single event-related EVP signal 90. The output of filter 88 is summed using a summer 92 with a stochastic white noise source 94, and input to an all-pole recursive filter 96 to output recorded EEG signal 98. The mathematical expression for this process relates the known recorded EEG signal samples, the EVP samples, the unknown coefficients (b1, b2 .... bM) for the non-recursive filter 88 and the unknown coefficients (a1, a2 .... aN) for the recursive filter 96 and the noise source 94. This expression may be solved for the filter coefficients (b1, b2, ... bM; a1, a2, ... aN) using the Batch Least Squares algorithm. This least-squares solution is asymptotically unbiased as long as the noise from the noise source 94 is uncorrelated.

Here, the EVP signal 98, input to the non-recursive filter 88, is assumed to be known in the least square solution process, and a well-established solution method such as an iterative process can be used. The iterative process considers the problem to be a sequence of such filter identifications. The iterative process starts with an appropriate event average evoked potential (EVP) response for the stimulus event as the initial deterministic input to the filter model. The filtered response is then estimated after the filter identification. The background-EEG component is obtained by subtracting the estimated filtered response from the EEG signal 98. The estimated response is then, in turn, input to the next iterative stage. This iterative process is repeated until the estimated responses converge to the evoked response.

The accuracy of the filter model identification at each iterative stage is evaluated by the whiteness of the estimated prediction error, determined from the cumulative Anderson test on the corresponding autocorrelation function. The predictor error is the residual between the measured EEG samples and the computed EEG values from the autoregressive moving average (ARMA) filter fit as shown in FIG. 6. The improvement in prediction error with iteration can be used to test for convergence.

Moreover, the convergence of the iterative process may be further ensured by comparing successive evoked response estimations for the EVP. This may be done using a correlator or linear matched filter in which the most recent estimation is the input, and the impulse response of the filter is the previous estimation reversed in time.

Equivalently, the successive estimations for the autoregressive coefficients (a1, a2 . . . . aN) for the background-EEG may be tested for convergence by using the predictor-residual ratio. This non-metric measure of the difference between the two different sets of coefficients is the logarithm of the ratio of the prediction residuals for the corresponding EEG sets. In turn, this is the logarithm of the ratio of matrix quadratic products of the computed EEG sample vectors, the correlation matrix, and the transpose of the vectors. This difference measure is derived from the logarithmic likelihood ratio which is the optimum statistical test that one set of coefficients is equivalent to another.

The logarithmic likelihood ratio reduces to the logarithm of the ratio of the prediction residuals for the two sets of samples. The residuals are the quadratic products of coefficient vectors and sample correlation matrix. The residuals are the linear prediction errors for the coefficient estimation process. The probability distribution governing the estimate of the true coefficients is multi-dimensional Gaussian. The mean values of the distribution are the true coefficient vector values. The covariance is computed from the coefficient vector and the correlation matrix of the EEG segments. Consequently, the difference measure is related to a Chi-square distribution. The product of the difference measure and the number of EEG samples is asymptotically a Chi-squared variate with degrees of freedom equal to the order (number of coefficients) of the autoregressive filter 96.

The final estimation for the EVP waveform is parameterized by the waveform components amplitudes and latencies and by the ARMA filter coefficients from the ARMA filter fit. In a further embodiment, an ARX model fit is conducted using the event average evoked potentials for both of the possible stimuli responses ("accept" and "reject"); the parameters and Anderson error from both fits are used to parameterize the waveforms for response classification.

Figure 7:
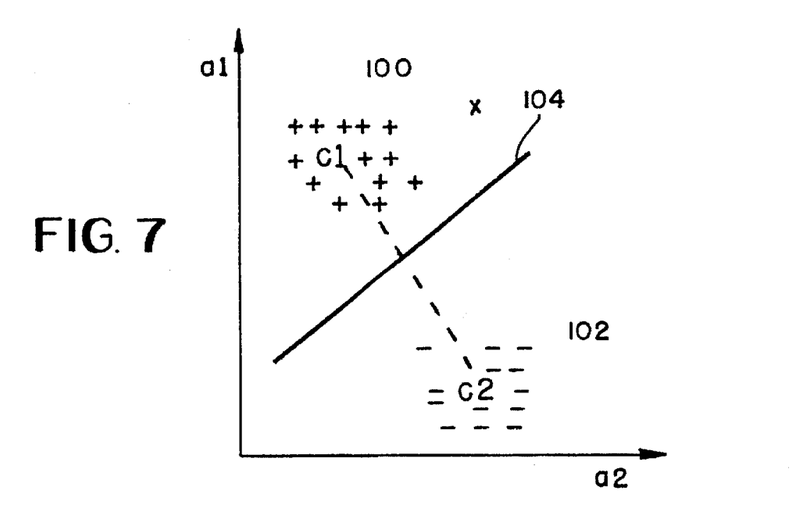
FIG. 7 is a diagram of a decision making response separability in a feature set space derived from fixation properties and evoked potential parameterization.

Still describing the routines of digital computer 18 and referring to FIGS. 4 and 7, the expert system routine 66 performs a classifying function by computing an estimate of the task-related selector decision from the eye gaze fixation properties and the parametric coefficients for the corresponding single event evoked potential. The routine 66 includes an expert front end routine 66a and a classification network 66b.

The expert front end routine 66a has embedded knowledge about the range of acceptable values for the fixation properties and evoked potential parameters. The front end routine 66a reviews the input data for extraneous values and smooths outliers accordingly. The classification network 66b serves as a two-category classifying statistical discriminant function, dividing a parametric feature set space into a region 100 for the "interest" decision response and another region 102 for the "no interest" response. The feature set space is defined by the parameters of the evoked potential (EVP) signal 84 representation (FIG. 5B) augmented by the fixation parameters, such as duration, pupil sizes, end state and gaze fixation number, related to the signal 78 (FIG. 5B).

The above-mentioned statistical discriminant function is a measure of the separability of the distributions of the features for the "interest" and "no interest" responses. The two regions 100,102 are separated by a decision surface 104 defined by a discriminant function. In this way, the discriminant problem is reduced from a multivariable one to a single variable by the discriminant mapping function. The mapping function maps the evoked signal features and the eye fixation properties to the discriminant dimension where the mapped value is compared to a threshold value. The decision is in one class if the function is greater than the threshold, and in the other class if not.

A powerful discriminant function, useful for representing the statistics of the decision making process, is an artificial neural network (ANN) based on Artificial Intelligence concepts. The artificial neural network (ANN) is a data-processing structure containing processing nodes which are fully integrated with one-way signal connections. Each processing node can take in data from many other processing nodes, but can only send data out in one direction. Such an output connection can branch to a number of other nodes with each connection carrying the same signal. Each input to a processing node is multiplied by a weight. All of the weighted inputs are then summed to determine the activation level of the processing node. Nearly all neural network architectures are based on this model.

Figure 8:
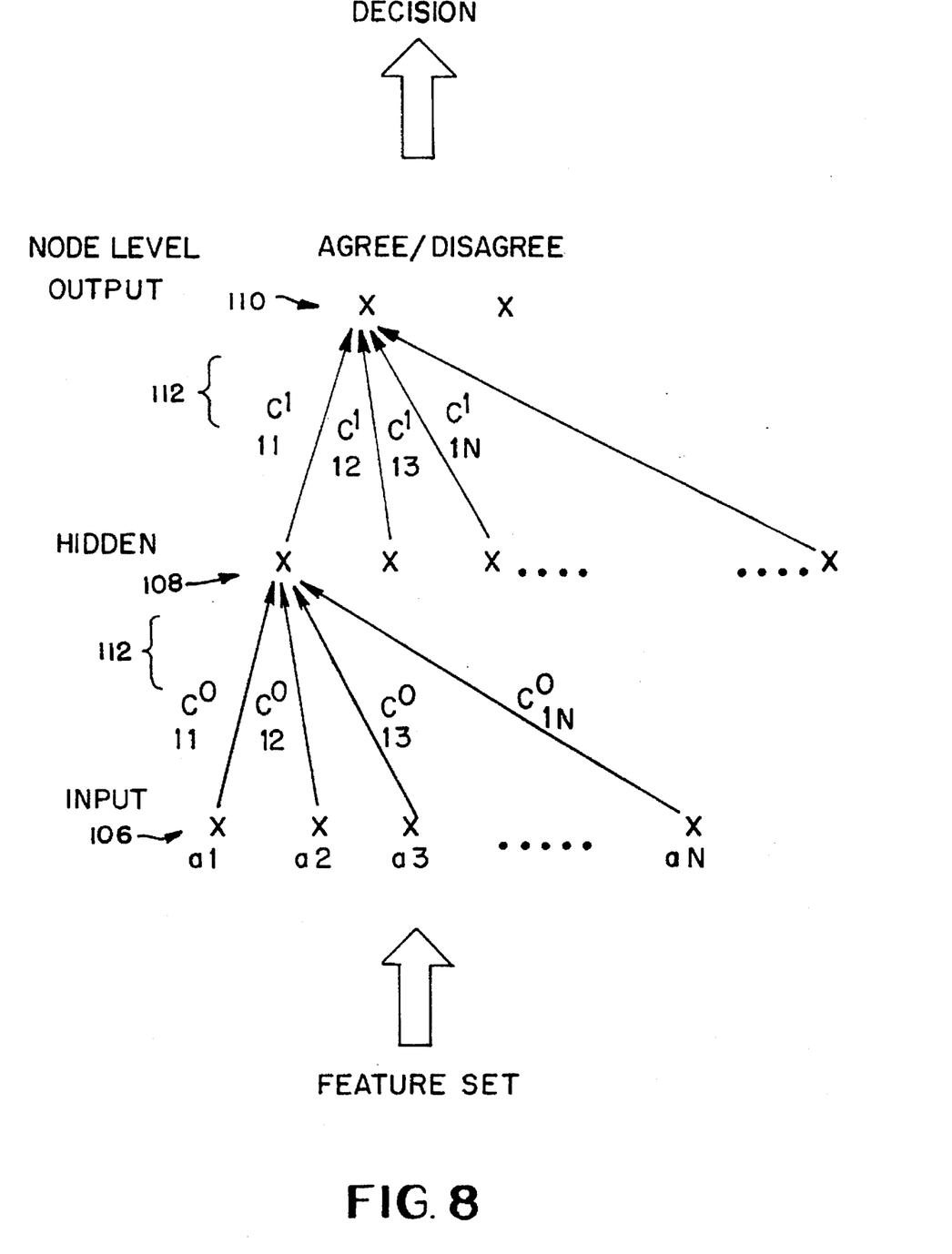
FIG. 8 is a schematic of an Artificial Neural Network (ANN) representation of a decision making mental process.

More specifically referring to FIG. 8, a highly successful artificial neural network is the Rumelhart's multilayer back-error propagation system. This type of system is a feedforward architecture that contains a layer of input neurons 106, one or more hidden layers of intermediate neurons 108, and a layer of output neurons 110, all interconnected with different weights 112. The network incorporates a supervised back-propagation method into which the weights 112 are adjusted using the difference in the actual output to the desired output for each training input set.

In a further embodiment, the classification network 66b of the computer routine 66 is an artificial neural network (ANN) with multiple-node input, hidden layers, back-error propagation, acting as a two node output classification machine. The inputs to the network are the front-end processed data for the fixation properties, such as duration, pupil sizes, end state and gaze fixation count, and the parameter set for the associated evoked potential, as represented by signal 84 in FIG. 5B, which is derived from the filter representation. Finally, the classification network 66b outputs the decision estimate, as interest or disinterest. Accordingly, the output of computer routine 66 represents an estimate of a mental decision for selecting the gaze point of regard.

Still referring to FIG. 4, the computer routine 70 of digital computer 18 computes the workspace eye gaze point of regard from the gaze viewing point and direction and a digitally stored data base on the workspace geometry. The viewed point in the user's visual workspace is computed using computer graphics concepts and a computer memory data base listing the objects and their locations in the user's workspace. The routine 70 computes the point of intersection of the gaze viewing direction with each workspace surface facing the user from the surface normal and the location of a vertex. The routine 70 checks to ensure that the intersection point is within the edges containing the surface. The viewed point is the contained intersection point closest to the user's eye. The positions and orientations of the surfaces of the objects in the user's visual workspace are listed in a digital memory computer data file by the directional cosines of their surfaces normals and the coordinates of the vertices. The surfaces of the objects are described by a piecewise net of planar segments for computational purposes.

Moreover, an automatic calibration method is used to compute certain user-specific constants for the filter functions of digital signal processor 38, the iterative process of computer routine 64, and the coefficients for the expert front end routine 66a and artificial neural network (ANN) 66b of computer routine 66. In using this method, the viewer first performs a sequence of muscular activities for brief periods while cerebral and artifact signals are measured. This establishes record files for the artifact signals as follows: (1) no activities for EKG, (2) tracking movements for EMG, (3) facial and head movements for EMG, and (4) finally visually tracking for EOGs. A set of regression analyses are then performed on the signal measurements to determine the parameters of the estimating and smoothing filters needed to isolate the electroencephalogramic (EEG) signal from the artifacts.

The viewer next looks at a series of display icons for which he has been instructed to designate as interest or disinterest while the viewing lines of sight, pupil sizes, skin surface potential measurements and his designation responses are recorded. The potential measurement data are then used to construct event average evoked potentials for the interest and disinterest responses. For each response, the electroencephalogramic signal is abstracted from the artifacts using estimating and smoothing filters; the eye fixation is isolated and the corresponding fixation duration is computed; and then the electroencephalogramic signal for the corresponding fixation duration is isolated. Finally, the electroencephalogramic (EEG) signals for equivalent responses are event averaged to estimate the average evoked potentials for the interest and disinterest cases.

In a further embodiment, Wiener filtering is used to refine the average evoked potentials for the interest and disinterest cases. The classical method of determining the visual evoked potential (VEP) is by ensemble averaging in which the evoked response to the same stimulus is summed over several hundred trials. In the ensemble averaging method, the variations in the background EEG are assumed to be cancelled, since they are not correlated with the stimulus, and large sample sizes are preferably used to reduce the estimation error to an acceptable level.

Therefore, the technique of Wiener filtering is more efficient than the ensemble averaging technique for determining the visual evoked potential (VEP) since fewer sample sizes are needed to reduce the estimation error to an acceptable level. In the Wiener filtering method, the Fourier transform of each individual sample EEG and the sample average of these Fourier transforms are computed by the Fast Fourier Transform. A frequency spectrum is constructed from the averaged Fourier transform to give the frequency spectrum of averaged EEG. Further, by making a frequency spectrum from the Fourier transform of each individual sample EEG and averaging them, a sample average of the frequency spectrum is obtained. An estimate of the Fourier transform of the filtered averaged VEP is computed from these quantities. The filtered averaged VEP is then obtained on a time line from the above estimate by the inverse Fast Fourier transform.

In a still further embodiment, a predictor-subtractor-restorer (PSR) filter is used to estimate the averaged visually evoked potentials (VEP) corrupted by background EEG. The PSR filter is known to be superior in performance to the Wiener filtering methods mentioned hereinabove. An autoregressive (AR) process model is fitted to the background EEG preceding the stimulus. The AR process model is then used to remove the background EEG from the post stimulus signal leaving an estimate of the altered evoked potential. An optimum inverse filter is then used to restore the averaged VEP from the residual. In theory, the optimum PSR filter and the noncausal Wiener filter are equivalent. However, in practice the described technique is reported to be superior in performance to the Wiener filter. The order of the AR-model is selected by finding the order where further increases in its value no longer cause a noticeable reduction in the variance of the prediction errors.

Following the determination of the average evoked potentials, the single event transient evoked potentials are computed for each designation test case, using the appropriate average evoked potential and the electroencephalogramic signal for the corresponding fixation duration. Finally, the parametric representations are computed for the set of single event transient evoked potentials. The optimal lengths of the filter model components are selected by minimizing the Akaike's functional Final Prediction Error. This represents a compromise proposed by Aikaike between the need of minimizing the power of the prediction error and the need of limiting the number of the parameters of the model.

The data set having the eye fixation properties, the parametric representations of the transient evoked potentials and the interest designations for each designation case, is used to train the artificial neural network (ANN) representing the interest-level. The values of the network weights appropriate for the classification problem are established during a supervised training period. The network is trained by a back-propagation method in which the weights are adjusted using the difference in the actual output to the desired output for each training input set. Initially, the weighting factors for the connections are set randomly. During the training phase, the weights are adjusted so that the difference between the output and a test answer supplied by the training routine is minimized. As the training progresses, the weights assigned to each interconnection between the processing nodes are iteratively changed so as to minimize the error to the desired answer.

Figure 9:
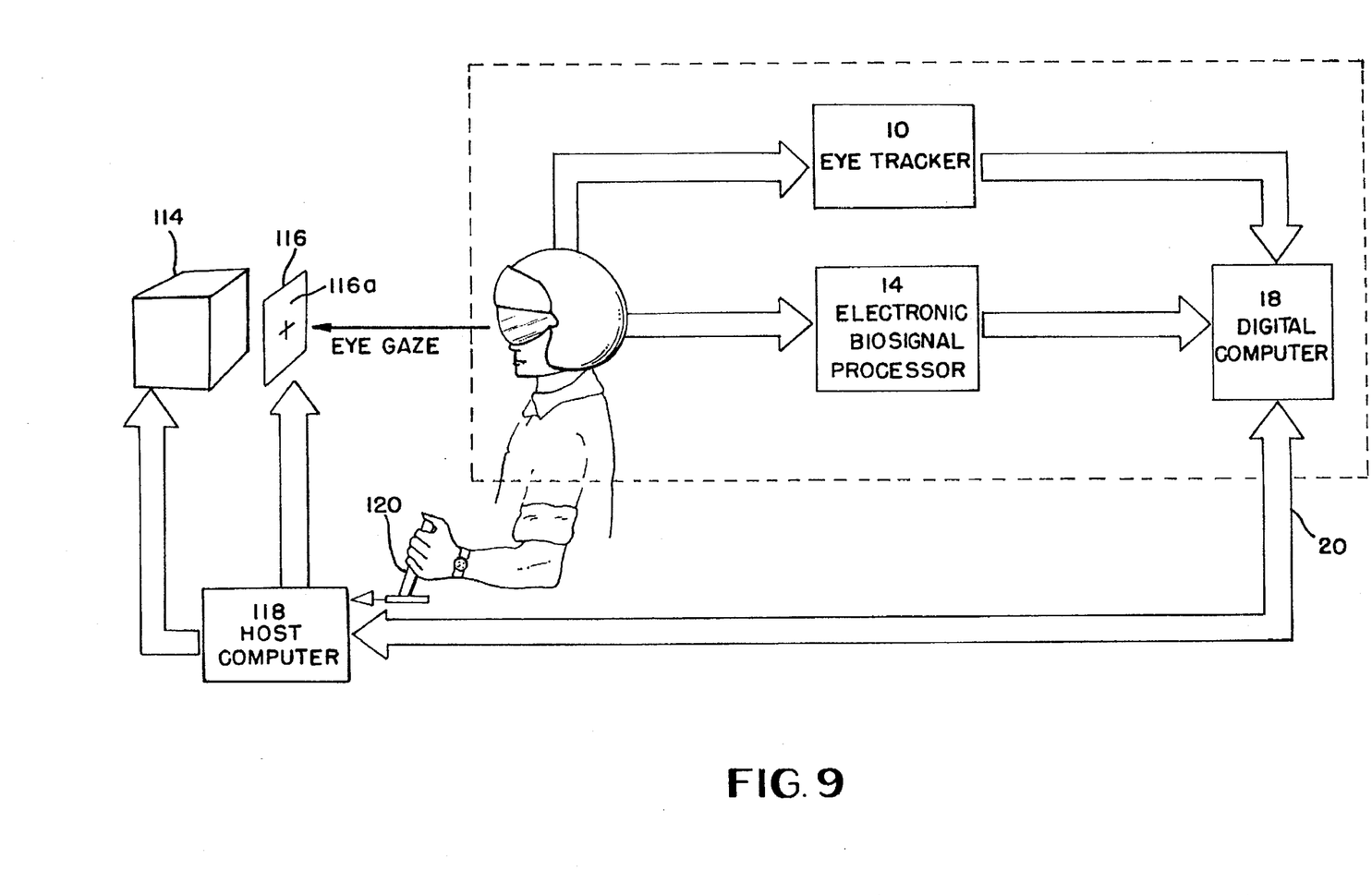
FIG. 9 is a schematic showing a computerized machine controlling system, according to one embodiment of the present invention.

Referring to FIG. 9, the present invention is exemplarily used to control computerized machinery 114 from a video display 116 by ocular gaze point of regard alone, by: (a) determining the interest level for a gaze point of regard using the eye tracker 10 and the biosignal processor 14; if selection is predicted from the output 20 of the digital computer 18, then (b) comparing the gaze point of regard to the locations of visual icons shown on the video display 116; if the point of regard is within a preselected distance to an icon 116a, then (c) executing the computer program routine on the host computer 118 corresponding to the selected icon 116a for machine control; and (d) updating the video display 116 to conform with the executed routine.

In a further embodiment, the routine 66 of digital computer 18 contains an on-line trainer 66c to refine the artificial neural network weights during applications. On-line training of the artificial neural network of routine 66 is performed following implementation of critical decisions requiring motor confirmation. For such decisions with severe consequences, such as engaging fire upon a suspected hostile, it would be required that the user confirm a select decision with a motor action such as a switch activation 120, before implementation. Thereafter, it is expected that the corresponding display icon will be momentarily enhanced by providing a feedback to the user following a "select" decision estimate. The confirming motor action 120 must be input to the host computer 118 and to the routine 66 of the computer 18 within a preselected time increment to preclude confoundment by further information processing or spurious actions, before the training state is activated. Following receipt of the confirming motor action 120, the evoked potential parameters and the fixation properties are used along with the original data base by the training component of routine 66 in supervised on-line reinforcement training of the network weights, using the back-error propagation method described hereinabove. The expert front end routine 66a of computer routine 66 has embedded knowledge about the range of reasonable values for the network weights to protect against erroneous training results.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for estimating a mental decision of a viewer for selecting a task, comprising ocular means for generating an ocular line of sight and pupil size of the viewer wherein;

said ocular means include:

measuring means for measuring an ocular viewing direction and pupil sizes of the viewer;

sensor means for measuring a head position and orientation of the viewer in a workspace; and digital processor means coupled with said measuring means and said sensor means, for computing and generating the ocular line of sight and pupil size data of the viewer in the workspace;

biosignal processor means for determining electroencephalogramic potential of the viewer;

said biosignal means include:

first electrode means for sensing scalp surface electroencephalogramic potentials from the cerebral scalp of the viewer; and first amplifying means for amplifying the sensed scalp surface electroencaphalogramic potentials;

second electrode means including a plurality of electrode sensors for generating extracerebral potential from body portions of the view; and third amplifying means including a plurality of amplifiers for respectively amplifying the generated extracerebral potentials;

the extracerebral potentials including electrooculogramic potentials generated by ocular processes, electromygramic potentials generated from facial throat, back, shoulder, and arm muscles of the viewer, and electrocardiogramic potentials generated from the heart of the viewer said biosignal processor means further include:

an analog-to-digital (A/D)converter, connected to said first and second amplifying means, for generating digital output signals of the scalp surface electroencephalogramic potentials and the extracerebral potentials; and a digital signal processor receiving the digital output signal from said A/D converter, said digital signal processor having first filtering means for filtering measurement noise from the digital output signals and second filtering means connected to said first filtering means for filtering attenuation from the digital output signals; and including summing means for summing the filtered digital output signals, so as to remove the electrooculogramic, electromygramic and electrocardiogramic potential from the scalp surface electroencephalogramic potentials;

computer means coupled to said ocular means and said biosignal processor means, for computing an estimate of the mental decision from the ocular line of sight and pupil size data and the electroencephalogramic potentials said computer means include:

a first computer routine which stores the ocular line of sight and pupil size data from said ocular means; and a second computer routine which determines if a sight state of the viewer is saccadic or fixation, using the ocular line of sight and pupil size data; wherein when the fixation is determined, said computer routine isolates the start and end of the fixation, computes s fixation duration, extracts the start and end pupil sizes, and determines a fixation end state and a gaze fixation count; wherein when the fixation is determined, said second computer routine determines values of fixation parameters and stores the fixation parameter values in memory;

a third computer means which stores the electroencephalogramic potential determined by said biosignal processor means; and a fourth computer routine which extracts a single event transient evoked potential for the fixation, from the starting and ending points of the fixation and using the stored electroencephalogramic potentials: and and computes a parametric representation of the single transient evoked potential using filter modeling techniques;

a fifth computer routine which generates workspace coordinate data of gaze point of regard of the viewer using the stored fixation parameter values; and a sixth computer routine which computes an estimate of the mental decision from an expert system employing an artifice neural network;

said artificial neural network representing a mental decision process and having eye gaze fixation properties and the parametric representation of the transit evoked potential as inputs.

2. The apparatus of claim 1, wherein said computer means outputs the estimate of the mental decision computed by said sixth computer routine and the workspace coordinate data of gaze point of regard generated by said fifth computer routine.

3. The apparatus of claim 1, wherein said second computer routine generates a service call for sequentially activating said fourth, fifth, and sixth computer routines.

4. A method for estimating a decision making process of selecting a workspace item for task implementation from an ocular gaze of a viewer alone, comprising:

computing a task-selection level for an ocular point of regard from a corresponding eye fixation duration and single event transient evoked potential including the steps of:

measuring cerebral and extracerebral signals from body portions of the viewer to establish record file for EHG, EMG, and EOG;

computing signals from the cerebral and extracerebral signals using a plurality of filters;

isolating the electroencephalogramic signals for a fixation duration of each interest and disinterest designation by the viewer;

estimating the average evoked potentials for the interest and disinterest designations using the electroencephalgramic signals;

refining the average evoked potentials using filtering techniques;

computing a transient evoked potential of each designation by the viewer using filter modeling techniques;

computing a parametric representation of the transient evoked potential;

training an artificial neural network using gaze fixation properties and parametric representation of the transient evoked potential to estimate the decision making process of the viewer; and b) determining that a selection decision is made for task implementation, if the computed task-selection level exceeds a threshold established by an artificial neural network.

5. The method of claim 4, further including the step of performing regression analyses to determine parameters of said plurality of filters in order to compute the electroencephalogramic signals from the cerebral and extracerebral signals.

* * * * *